(12) United States Patent
Faustman

(10) Patent No.: US 8,969,015 B2
(45) Date of Patent: Mar. 3, 2015

(54) METHODS AND KITS FOR DIAGNOSING SJÖGREN'S SYNDROME

(71) Applicant: The General Hospital Corporation, Boston, MA (US)

(72) Inventor: Denise L. Faustman, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/078,020

(22) Filed: Nov. 12, 2013

(65) Prior Publication Data

US 2014/0134644 A1    May 15, 2014

Related U.S. Application Data

(60) Provisional application No. 61/724,787, filed on Nov. 9, 2012.

(51) Int. Cl.
*G01N 33/53* (2006.01)
*G01N 33/564* (2006.01)

(52) U.S. Cl.
CPC ........ *G01N 33/564* (2013.01); *G01N 2333/912* (2013.01); *G01N 2440/14* (2013.01); *G01N 2440/36* (2013.01); *G01N 2800/101* (2013.01)
USPC ............................................. 435/7.1; 435/7.2

(58) Field of Classification Search
None
See application file for complete search history.

(56) References Cited

U.S. PATENT DOCUMENTS

| 7,582,313 | B2 | 9/2009 | Faustman |
| 7,628,988 | B2 | 12/2009 | Faustman |
| 8,017,392 | B2 | 9/2011 | Faustman |
| 8,021,693 | B2 | 9/2011 | Faustman |
| 8,173,129 | B2 | 5/2012 | Faustman |
| 8,697,077 | B2 | 4/2014 | Faustman |
| 2009/0233268 | A1 | 9/2009 | Lin et al. |
| 2012/0171221 | A1 | 7/2012 | Hamm-Alvarez et al. |

FOREIGN PATENT DOCUMENTS

WO    WO-2004/003164 A2    1/2004

OTHER PUBLICATIONS

Enzo Life Science 2003 Antibody information (part, total 4 pages).*
Krause et al. (Ann Rheum Dis 2006 vol. 65, p. 1021-1027).*
Morawietz et al. (J. Rheumatol. 2009 vol. 36, p. 2694-2703.*
Eleftheriadis et al., "Major histocompatibility complex class I restricted T-cell autoreactivity in human peripheral blood mononuclear cells," Cell Immunol. 240(1):62-7 (2006).
International Search Report for International Application No. PCT/US13/69744 mailed Apr. 16, 2014 (7pages).
Mishto et al., "Immunoproteasome and LMP2 polymorphism in aged and Alzheimer's disease brains," Neurobiol Aging. 27(1):54-66 (2006).
Sibille et al., "LMP2+ proteasomes are required for the presentation of specific antigens to cytotoxic T lymphocytes," Curr Biol. 5(8):923-30 (1995).
Song et al.,"Novel autoimmune hepatitis-specific autoantigens identified using protein microarray technology," available in PMC Jan. 1, 2011, published in final edited form as J Proteome Res. 9(1):30-9 (2010).
Written Opinion of the International Searching Authority for International Application No. PCT/US13/69744 mailed Apr. 16, 2014 (17 pages).

* cited by examiner

*Primary Examiner* — Jacob Cheu
(74) *Attorney, Agent, or Firm* — Clark & Elbing LLP; Paul T. Clark, Esq.; Todd Armstrong

(57) ABSTRACT

The invention features methods and kits for determining the presence of, or a predisposition to develop, Sjögren's syndrome in humans. The invention features methods to detect changes in the levels of one or more LMP-2 protein isoforms, in particular phosphorylated isoforms of LMP-2, and to detect changes in cellular protein phosphorylation and ubiquitination in samples from Sjögren's patients.

20 Claims, 11 Drawing Sheets

Figure 3B

| Sample | Primary | LMP2 |
|---|---|---|
| 4 | anti-LMP2 | 227 |
| 6 | anti-LMP2 | 362 |
| 27 | anti-LMP2 | 358 |
| 37 | anti-LMP2 | 224 |
| 40 | anti-LMP2 | 342 |
| 42 | anti-LMP2 | 928 |

Figure 8

| Sample | Primary | Capillary | Peak 1 | Peak 2 | Peak 3 | Peak 4 |
|---|---|---|---|---|---|---|
| Sample 4 | ERK 1/2 | C3:1 | 2,657 | 6,308 | 7,405 | 4,983 |
| Sample 4 | ERK 1/2 | C3:2 | 2,203 | 5,918 | 6,008 | 4,372 |
| Sample 6 | ERK 1/2 | C3:3 | 884 | 2,596 | 5,086 | 2,179 |
| Sample 6 | ERK 1/2 | C3:4 | 938 | 3,103 | 5,531 | 2,336 |
| Sample 27 | ERK 1/2 | C3:5 | 898 | 1,354 | 1,048 | 6,641 |
| Sample 27 | ERK 1/2 | C3:6 | 931 | 1,777 | 1,495 | 7,411 |
| Sample 37 | ERK 1/2 | C3:7 | 670 | 676 | 1,004 | 6,355 |
| Sample 37 | ERK 1/2 | C3:8 | 610 | 757 | 1,078 | 7,558 |
| Sample 40 | ERK 1/2 | C3:9 | 1,092 | 2,655 | 7,566 | 6,380 |
| Sample 40 | ERK 1/2 | C3:10 | 1,311 | 3,184 | 8,870 | 5,701 |
| Sample 42 | ERK 1/2 | C3:11 | 5,638 | 7,171 | 5,865 | 1,522 |
| Sample 42 | ERK 1/2 | C3:12 | 6,426 | 7,713 | 5,643 | 1,692 |

METHODS AND KITS FOR DIAGNOSING SJÖGREN'S SYNDROME

FIELD OF THE INVENTION

The invention features methods and kits for diagnosing Sjögren's syndrome.

BACKGROUND OF THE INVENTION

Sjögren's syndrome affects up to 4 million people in the United States, 90% of whom are women. Patients with this autoimmune disease, which targets and destroys exocrine glands, such as the tear (lacrimal) and salivary glands, often experience the classic symptoms of severe dry mouth and/or eyes. Patients with Sjögren's syndrome are at an increased risk of infection and/or damage to these organs (e.g. corneal scarring, dental decay, gingivitis). They may also experience complications related to the destruction of other moisture-producing glands, or have systemic complications, such as disabling fatigue, joint pain and stiffness, or dysfunction of the heart, blood vessels, lung, liver, nerves, or kidney. Currently, there is no cure for Sjögren's syndrome. Treatment is focused on symptom relief and on prevention and treatment of complications.

As with many other autoimmune diseases, the underlying cause of Sjögren's syndrome is driven in part by the presence of abnormal T cells that are reactive to self proteins. Although diverse animal models are studied in Sjögren's syndrome, the non-obese diabetic (NOD) murine model of spontaneous diabetes and Sjögren's syndrome is frequently studied to understand early T cell education pathways that contribute to disease. NOD mice clinically show symptoms similar to human Sjögren's syndrome, such as reduced saliva production, presence of lymphocytic infiltrates in the salivary glands, and genetic linkage of the disease to the gene cluster known in the human as the MHC (HLA) class II region. The MHC region contains not only the HLA class II genes themselves, but a diversity of MHC class I processing genes, such as Tap (Ham) and the LMP genes (e.g., LMP-2, LMP-7). The LMP genes and proteins are part of the cytoplasmic proteasome complex (FIG. 1) that acts as a protein processing station by taking long peptides and breaking them into fragments that allow MHC class I assembly into the class I exterior facing groove. Originally, the MHC class I processing gene was thought to have an exclusive role in peptide presentation for host defense during intracellular viral infections. Later it was discovered that antigen presenting cells have defects in MHC class I assembly in the NOD mice and in humans with autoimmunity. Further studies of the MHC class I pathway in the NOD mice revealed that the interrupted antigen processing was due to the lack of production of the LMP-2 proteasome protein in the immune system in young mice progressing towards disease.

Diagnosis of Sjögren's syndrome is based on a combination of blood tests, tissue studies (e.g., salivary gland biopsy), and physical exams to detect symptoms. In general, a positive diagnosis involves having at least 4 out of 6 symptoms from a list that includes dry mouth, dry eye, ocular involvement, evidence of lymphocytic infiltrates into the minor salivary glands (through lip biopsy), impaired salivary gland function, and serum autoantibodies against Ro[SSA] and/or La[SSB] antigens. This diagnostic system is imprecise, with a significant false negative rate owing to lip biopsies that miss small, early sites of inflammation and low-titer autoantibody tests. In addition, lip biopsy is undesirable for many patients, since it may cause disfigurement or additional damage to an organ that is already dysfunctional.

Thus, there is a need for effective diagnostic tests for Sjögren's syndrome that improve detection of this difficult-to-diagnose disease.

SUMMARY OF THE INVENTION

The invention features a method for determining the presence of, or a predisposition to develop, Sjögren's syndrome in a human comprising: obtaining a sample from the human; and measuring the level of one or more LMP-2 protein isoforms in the sample using isoelectric focusing comprising separation of proteins based on pI or pH, wherein the LMP-2 protein isoforms have a pI in the range of 4.5-5.5, and wherein a reduction in the level of at least one LMP-2 protein isoform relative to a control sample is indicative of the presence of, or a predisposition to develop, Sjögren's syndrome. In one aspect of the invention, the method further comprises a molecular weight resolution step.

In a preferred embodiment isoelectric focusing is performed by separation of proteins in a pI gradient or a pH gradient, in the absence of a molecular weight resolution step. In yet another aspect, the method further comprises using western blot assay using an anti-LMP-2 antibody for measuring the level of one or more LMP-2 protein isoforms.

The invention also features a method for determining the presence of, or a predisposition to develop, Sjögren's syndrome in a human comprising: obtaining a sample from the human; and measuring the level of one or more LMP-2 protein isoforms in the sample using an anti-LMP-2 antibody, wherein the LMP-2 protein isoforms have a molecular weight in the range of 21-23 kD, and wherein a reduction in the level of the at least one LMP-2 protein isoform relative to a control sample is indicative of the presence of, or a predisposition to develop, Sjögren's syndrome. In one aspect of the method, the method is performed using an immunoassay. The immunoassay is selected from the group consisting of western blot assay, ELISA, pH or pI gradient electrophoresis, gel electrophoresis, or radioimmunoassay.

In the above mentioned method, the antibody to be used can be a monoclonal or polyclonal antibody. The polyclonal antibody is one of LMP2(N-20) or LMP2(C-20). The monoclonal antibody is one of LMP2-13 or MCP421.

In one aspect of the invention, the method involves measuring the level of two, three, or four of the LMP-2 protein isoforms. In another aspect of the invention, the method involves detecting LMP-2 protein isoforms that are differentially phosphorylated. The differentially phosphorylated isoforms have different charges and can be detected and separated using a pI/pH gradient.

In one aspect of the methods of the invention, the reduction in LMP-2 protein isoform levels is at least a 20% (e.g., 20%, 25%, 30%, 35%, 40%, 50%, 60%, 70%, 80%, or 90% or more) reduction in the level of at least one or more of the LMP-2 protein isoforms in the sample relative to a control sample.

In another aspect of the invention, the methods of the invention further comprise measuring the change in phosphorylation of one or more proteins in the sample relative to a control sample. These proteins can be one or more of intracellular proteins that are degraded by the proteasome. The proteins can be ERK1 or ERK2 and the change that is measured can be an increase in phosphorylation of ERK1 or ERK2 protein. In another aspect of the invention, the methods of the invention further comprise measuring an increase in ubiquitination of one or more proteins in the sample relative to a control sample.

The invention features a method for determining the presence of, or a predisposition to develop, Sjögren's syndrome in a human comprising: obtaining a sample from the human; and measuring a change in phosphorylation of one or more proteins in the sample relative to a control sample, wherein a change of at least 10% (e.g., 10%, 20%, 25%, 30%, 35%, 40%, 50%, 60%, 70%, 80%, or 90% or more) in the sample is indicative of the presence of, or a predisposition to develop Sjögren's syndrome. In one aspect of the above method, the increase in phosphorylation of ERK1 or ERK proteins is measured.

The invention also features a method for determining the presence of, or a predisposition to develop, Sjögren's syndrome in a human comprising: obtaining a sample from the human; and measuring an increase in ubiquitination of one or more proteins in the sample relative to a control sample, wherein an increase in the level of ubiquitinated proteins of at least 10% (e.g., 20%, 25%, 30%, 35%, 40%, 50%, 60%, 70%, 80%, or 90% or more) in the sample is indicative of the presence of, or a predisposition to develop Sjögren's syndrome.

In the above methods, the human has, or is suspected of having, Sjögren's syndrome.

The invention also features a kit for determining presence of, or a predisposition to develop, Sjögren's syndrome in a human comprising: a) a lysis buffer; b) one or more anti-LMP-2 antibodies; and c) instructions for using the lysis buffer to lyse cells in a sample obtained from the human and for using the one or more antibodies in an immunoassay to detect a reduction in a level of one or more LMP-2 protein isoforms in the sample relative to a control sample, and wherein the reduction in one or more LMP-2 protein isoforms indicates the presence of, or a predisposition to develop, Sjögren's syndrome in the human.

In one aspect of the kit, the immunoassay is selected from the group consisting of western blot assay, pH or pI gradient electrophoresis, gel electrophoresis, ELISA, and radioimmunoassay. In another aspect of the kit, the lysis buffer is selected from a group consisting of a Bicine/CHAPS buffer, a RIPA buffer, and a urea-based lysis buffer and combinations thereof.

In yet another aspect of the kit, the antibody of the kit is a monoclonal or a polyclonal antibody, wherein the polyclonal antibody is one of LMP2(N-20) or LMP2(C-20) and the monoclonal antibody is one of LMP2-13 or MCP421.

In one aspect the invention also features buffers for performing the methods of the invention and for use in the kit of the invention. In particular, the buffer is the "Limei" buffer described herein.

In the above methods and kit, the sample can be sweat, tears, urine, saliva, semen, serum, plasma, cerebrospinal fluid (CSF), feces, vaginal fluid, sputum, nasopharyngeal aspirate or swab, blood, peripheral blood lymphocytes (PBLs), lymphocytes, lymphocyte subsets (CD4, CD8, T cells, B cells, dendritic cells, monocytes, macrophages, and/or neutrophils), and lacrimal fluid. The sample can also be mucous or epithelial swab (buccal swab), tissues, organs, bones, teeth, and tumors. Preferably the body fluid or tissue includes lymphocytes. The samples can be obtained from a human not having Sjögren's syndrome (control sample), a human suspected of having Sjögren's syndrome, or a human diagnosed with Sjögren's syndrome.

"Control" as used herein refers to a sample from a human without Sjögren's syndrome, with no history of Sjögren's syndrome, and no history of any autoimmune disease.

"Isoelectric focusing" as used herein refers to a method of separating proteins in a sample using pI or a pH gradient gel electrophoresis, which separates proteins based on their charge or phosphorylation state. The isoelectric focusing step can be, optionally, followed by an additional resolution step that may include e.g., separating the proteins based on molecular weight.

"Reduction in the level" as used herein refers to a decrease in the amount of one or more LMP-2 protein isoforms (e.g., one or more phosphorylated isoforms of LMP-2) in a patient sample as compared to the level of those isoforms in a control sample.

"Sample" as used herein refers to a body fluid or tissue. Examples include sweat, tears, urine, saliva, semen, serum, plasma, cerebrospinal fluid (CSF), feces, vaginal fluid, sputum, nasopharyngeal aspirate or swab, blood, peripheral blood lymphocytes (PBLs), lymphocytes, lymphocyte subsets (CD4, CD8, T cells, B cells, monocytes, macrophages, and/or neutrophils), and lacrimal fluid. The sample can also be mucous or epithelial swab (buccal swab), tissues, organs, bones, teeth, and tumors. Preferably the body fluid or tissue includes lymphocytes (e.g., macrophages, monocytes, B lymphocytes, and dendritic cells). The samples can be obtained from a human not having Sjögren's syndrome (control sample), a human suspected of having Sjögren's syndrome, or a human diagnosed with Sjögren's syndrome.

BRIEF DESCRIPTION OF THE DRAWINGS

FIG. 3B shows the quantitation of the data from FIG. 3A.

FIG. 8 shows the quantitation of the data shown in FIG. 6.

DETAILED DESCRIPTION OF THE INVENTION

Figure 1:
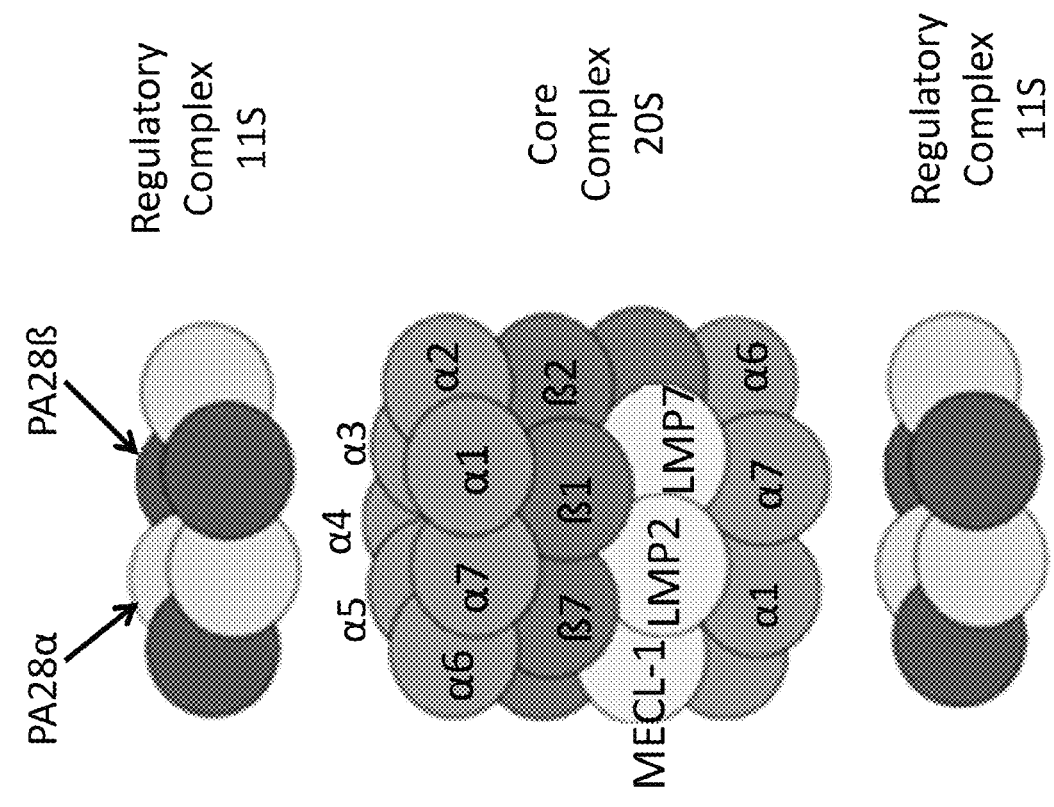
FIG. 1 is a schematic representation of the proteasome, which is a multi-subunit structure, found in the cytoplasm of immune cells and essential for protein processing of self-peptides and cytoplasmically located viral peptides during infections. For T cell education, the proteasome turns into an immuno-proteasome; the MHC class II encoded LMP-2, LMP-2 and MECL-1 unit are incorporated; and self-peptides are efficiently prepared for MHC class I assembly.

The present invention features a novel diagnostic for Sjögren's syndrome in patients with primary disease (i.e., having no other rheumatic conditions) based on detection of LMP2 protein isoforms (e.g., LMP-2 phosphoprotein isoforms) in a standard blood sample. Development of a more specific diagnostic for Sjögren's syndrome will aid in earlier diagnosis and treatment of this disease, and an attendant reduction in healthcare costs associated with disease progression and complications.

In humans, up until now, only two isoforms of the LMP-2 protein had been identified by molecular weight determinations. Surprisingly, we have identified at least four and perhaps five LMP-2 isoforms and have determined that each of these isoforms is reduced in Sjögren's syndrome patients. Accordingly, detection of a reduction in LMP-2 protein isoform expression can be used as a diagnostic marker for Sjögren's syndrome. This additional isoform diversity is from phosphorylation diversity detectable by changes in the pH or pI of the protein.

The invention features methods, and kits for diagnosing Sjögren's syndrome in human patients with primary disease (i.e., having no other rheumatic conditions) by detecting changes in the levels of 1, 2, 3, or 4 or more LMP-2 protein isoforms, e.g., LMP-2 phosphoprotein isoforms, (or ratios of these isoforms) in a body tissue or fluid sample of a patient relative to a control sample. The invention also features methods for measuring changes in phosphorylation and/or ubiquitination of cellular proteins for diagnosing Sjögren's syndrome in human patients. The invention also features a kit for diagnosing Sjögren's syndrome in human patients.

Methods for Diagnosis of Sjögren's Syndrome

The invention features several methods for detecting LMP-2 protein isoforms and changes in the levels of these isoforms in patient samples, and methods for detecting changes in phosphorylation and/or ubiquitination of cellular proteins for diagnosing Sjögren's syndrome in human patients. These methods are described below.

Diagnostic Assay Using pI or pH Gradients

The invention features a method for diagnosing Sjögren's syndrome in a human patient by detecting the levels of one or more LMP-2 protein isoforms (e.g., LMP-2 phosphoprotein isoforms) in a sample from the patient using, e.g., phosphoprotein detection. By isoforms is meant the phosphorylated isoforms of LMP-2 protein. Phosphoproteins can be separated from each other by charge differences detectable in pH or pI gradients. This assay is used to detect a reduction in the level of, or a change in the ratio of, one or more (e.g., 1, 2, 3, or 4 or more) LMP-2 isoforms in the sample. One method to separate proteins based on charge differences is by isoelectric focusing. Methods for performing isoelectric focusing to separate proteins based on pI or pH are well known in the art (see e.g., U.S. patent application publication No. 20050102629, incorporated herein by reference). The LMP-2 protein isoforms can have a pI in the range of 4.5-5.5 (e.g., 4.5, 5, or 5.5). A reduction in the level of one or more of the LMP-2 protein isoforms relative to the level of one or more of the LMP-2 isoforms in a control sample is indicative of the presence of, or a predisposition to develop, Sjögren's syndrome. The reduction in LMP-2 protein isoform level in a patient sample is at least 25%, more preferably at least 50% (e.g., 20%, 25%, 30%, 35%, 40%, 50%, 60%, 70%, 80%, or 90% or more) as compared to the expression level of the LMP-2 isoforms in a control sample. The control sample is preferably obtained from a human without Sjögren's syndrome. If necessary, the isoelectric focusing step can be followed by other method steps. This may include separation of proteins based on molecular weight and/or western-blot assay. Preferably the detection of one or more LMP-2 isoforms occurs by using an anti-LMP-2 antibody, such as those described herein.

Diagnostic Assay Using Immunoassay

The invention also features a method for diagnosing Sjögren's syndrome by detecting the levels of one or more LMP-2 protein isoforms in a sample from the patient using an immunoassay. Preferably the immunoassay involves the use of an antibody that can detect one or more (e.g., 1, 2, 3, or 4) LMP-2 protein isoforms in a patient sample. The immunoassay can be a western-blot assay, an ELISA, or a radioimmunoassay. The immunoassay detects one or more LMP-2 isoforms having a molecular weight in the range of 21-24 kD (for e.g., 21, 21.5, 22, 22.5, 23, 23.5, or 24 kD). A reduction in the level of, or a change in the ratio of, one or more of the LMP-2 protein isoforms relative to the level, or ratio, of one or more of the LMP-2 isoforms in a control sample is indicative of the presence of, or a predisposition to develop, Sjögren's syndrome. The reduction in LMP-2 protein isoform level in patient sample is at least 25%, more preferably at least 50% (e.g., 20%, 25%, 30%, 35%, 40%, 50%, 60%, 70%, 80%, or 90% or more) as compared to the expression level of the LMP-2 isoforms in a control sample. The control sample is preferably obtained from a human without Sjögren's syndrome.

The LMP-2 isoforms may be differentially phosphorylated. In this case their detection would not be by molecular weight but by using analysis techniques that allow phosphoprotein separations. Phosphoproteins are commonly separated by pI or pH differences because the addition of each phosphate makes the protein more acidic. For example, of the four to five LMP-2 isoforms, it is possible that some are phosphorylated, while others are not phosphorylated. Alternatively, it is possible that each isoform is phosphorylated to a different degree, which gives rise to differences in molecular weight and pI in the immunoassay using a specific phospho-detecting antibody or in a gradient that separates by pH or pI.

Diagnostic Assay Using Phosphorylation Status as an Indicator

The invention features a method for diagnosing Sjögren's syndrome by detecting a change in phosphorylation of one or more proteins in a patient sample relative to a control sample. This change can be an increase or a decrease in the amount of phosphorylated proteins in the patient sample. Preferably, this change is an increase or decrease in the amount of phosphorylated proteins of at least 10% (e.g., 10%, 15%, 25%, 35%, 50%, 75%, 90%, or more) in the patient sample, relative to the control sample. Preferably the change is an increase in the amount of phosphorylated proteins. This change in phosphorylation can be measured using an immunoassay, e.g., western blot assay, ELISA, or a radioimmunoassay. Preferably, the method involves measuring an increase in phosphorylation of ERK1 or ERK2 (e.g., using a western blot assay using an anti-phospho-ERK antibody) in the patient sample relative to a control sample. One can further distinguish proteins by pH or pI in a phospho-assay.

Diagnostic Assay Using Ubiquitination Status as an Indicator

The invention features a method for diagnosing Sjögren's syndrome by detecting an increase in ubiquitination of one or more proteins in a patient sample relative to a control sample. Preferably, this increase is at least a 10% (e.g. 10%, 25%, 35%, 50%, 75%, 90%, or more) increase in ubiquitination in the patient sample, relative to the control sample. Proteins that are not rapidly processed in the cytoplasm of the cells due to a proteasome dysfunction will by slowly degraded and thus in this slowed state the proteins will become over-ubiquitinated. Preferably, the method involves detecting an overall increase in the amount of ubiquitination of proteins in a cell population (e.g., a population of peripheral blood mononucleocytes (PBLs) or in macrophages, monocytes, B lymphocytes, T cells and dendritic cells) present in a patient sample relative to a control sample. This increase in ubiquitination can be measured using an immunoassay, e.g., western blot assay, ELISA, or a radioimmunoassay. An anti-ubiquitin antibody can be used in a western blot assay to measure increase in ubiquitination of proteins.

Combination Assays

In further aspects of the method of the invention, the immunoassay and the isoelectric focusing assay can be combined with additional assays as part of the diagnostic methods. For example, the additional assay can be measuring the change in phosphorylation of one or more proteins (e.g., ERK1 or ERK2) in the patient sample relative to the control sample, as described above. In another aspect, the additional assay can be measuring an increase in ubiquitination of one or more proteins in the patient sample relative to the control sample, as described above.

Kit for Diagnosis of Sjögren's Syndrome

The invention features a kit for diagnosis of Sjögren's syndrome that includes: a lysis buffer; one or more anti-LMP-2 antibodies that can be used to detect LMP-2 protein isoforms; and instructions for using the lysis buffers to lyse cells in a sample obtained from a human; instructions for using the antibodies to detect a reduction in the level of, or a change in the ratio of, one or more (e.g., 2, 3, or 4 or more) LMP-2 protein isoforms (e.g., LMP-2 phosphoprotein isoforms) in the sample relative to a control sample. The sample to be processed by the kit can be a body tissue or fluid as described above, preferably one that includes lymphocytes (e.g., macrophages, monocytes, B lymphocytes, and/or dendritic cells).

The lysis buffer of the kit can be any one of, or a variant of any one of, a Bicine/CHAPS buffer, a RIPA buffer, or a urea-based lysis buffer ("Limer" buffer). Typical compositions of these buffers are described below.

Bicine/CHAPS Lysis Buffer

Typical formulation of the Bicine/CHAPS lysis buffer used in the invention can include 150 mM NaCl, 10 mM Bicine, pH 8.2 containing 1% CHAPS. The concentration of NaCl can range from 130 mM to 165 mM (e.g., 130 mM, 140 mM, 150 mM, 160 mM, or 165 mM). The concentration of Bicine can range from 5 mM to 25 mM (e.g., 5, 10, 15, 20, or 25 mM). In addition, the concentration of CHAPS can range from 0.5% to 2% (e.g., 0.5%. 0.8%, 1%, 1.5%, 1.8%, or 2%). The pH of the buffer can range from 7.4-8.5 (e.g., pH of 7.4, 7.6, 7.8, 8, 8.2, 8.4, or 8.5). The lysis buffer can be optimized to have an aqueous inhibitor, and a DMSO inhibitor. The sample can be sonicated to get an even representation of the cellular proteins.

RIPA Lysis Buffer

RIPA lysis buffer is composed of 1×RIPA Buffer: 20 mM Tris-HCl (pH 7.5), 150 mM NaCl, 1 mM $Na_2$EDTA, 1 mM EGTA, 1% NP-40, 1% sodium deoxycholate, 2.5 mM sodium pyrophosphate, 1 mM b-glycerophosphate, 1 mM $Na3VO_4$ and 1 µg/ml leupeptin. Other formulations of RIPA lysis buffer used in the invention can include 50 mM Tris, 150 mM NaCl, 0.1% SDS (e.g., 0.025%, 0.05%, 0.1%, 0.5%, or 1%) sodium deoxycholate, and 1% (e.g., 0.5%, 1%, or 2%) Triton X-100. Alternatively, 10 mM sodium phosphate can be used instead of 50 mM Tris. With regard to the detergent, NP-40 can be used instead of Triton X-100. The concentration of NaCl can range from 130 mM to 165 mM (e.g., 130 mM, 140 mM, 150 mM, 160 mM, or 165 mM). The concentration of Tris can range from 15 mM to 60 mM (e.g., 15 mM, 20 mM, 30 mM, 35 mM, 40 mM, 45 mM, 50 mM, 55 mM, or 60 mM).

Urea Based Lysis Buffer ("Limei" Buffer)

For preparation of buffers containing urea, the denaturant is weighed and 2 M imidazole and 1 M Tris-HCl (pH 8.0), are added followed by $H_2O$ to 90% of the final volume. The container is heated and then cooled by the solubilization process of the denaturant, to room temperature in a water bath at 45° C. while stirring. The denaturant dissolves within minutes. Alternatively, the solution is stirred overnight at room temperature. The pH is adjusted at room temperature, the final volume is brought up with water and the solution is then filtered. 2-mercaptoethanol is added immediately prior to use if denaturation of proteins is desired. De-phosphorylation inhibitors are added to prevent the loss of phosphate groups from the separated proteins.

Lysis buffers are used as follows. Cells are washed with 10 mL of ice-cold PBS (Cellgro, cat#21-031-CV) and wells are aspirated. 400 uL of ice-cold lysis buffer is added to a 10 cm plate placed on ice. The plate is swirled to ensure good liquid coverage and incubated for 10 minutes on ice. The plate is then scraped and the solution is pipeted up and down to mix. The lysate is transferred to a microfuge tube and ells are lysed for an additional 30 minutes. The lysate is clarified by centrifugation (at 14,000 g for 15 minutes) in a cooled centrifuge. The supernatant is transferred to a fresh microfuge tube. The supernatant is immediately aliquoted (10-30 uL) on ice and snap freeze on dry ice.

Samples are typically loaded on a 384-well plate for microcapillary detection of molecular weight or micro-capillary detection of phosphorylation patterns as follows. Protein concentration is typically at 0.05 mg/mL final in capillary by BCA assay. The following components are used in this assay format:

a) sample diluent: Bicine/CHAPS Lysis Buffer (Cell Biosciences, p/n 040-764) plus 1×DMSO Inhibitor;
b) mix: ampholyte premix: Premix 5-8 (Cell Biosciences Premix G1, p/n 040-327 or Premix G2, p/n 040-973) pI standards: pI Standard Ladder 3 (Cell Biosciences, p/n 040-646);
c) wash: Wash Buffer (Cell Biosciences, p/n 040-654);
d) primary antibody: anti-ERK1/2 (Millipore, cat#06-182), 1:200 and anti-phospho ERK (Cell Signaling Technology, cat#9101 or cat#4377), 1:50 in Antibody Diluent (Cell Biosciences, p/n 040-309);
e) detection antibody: anti-Rabbit HRP (Cell Biosciences, p/n 040-656), 1:100 in Antibody Diluent;
f) Anolyte: Phosphoric Acid, 10 mM (Cell Biosciences, p/n 040-650);
g) Catholyte: Sodium Hydroxide, 100 mM (Cell Biosciences, p/n 040-651); and
h) Luminol/Peroxide: mixed 1:1 (Cell Biosciences, p/n 040-652 and p/n 040-653)

The conditions for separations of proteins in a micro-capillary tube including a pH separation typically employs a NanoPro 1000 system and the following parameters: sample loading time: 10 seconds (Premix G1), 25 seconds (Premix G2); focus conditions: 15000 µW, 40 minutes (Premix G1) or 21000 µW, 40 minutes (Premix G2), Immobilization: 80 seconds; wash 1: 2×150 seconds (default); primary antibody incubation: 120 minutes; wash 2: 2×150 seconds (default); detection antibody incubation: 60 minutes; wash 3: 2×150 seconds (default); and chemiluminescence exposure: 60, 120, and 240 seconds.

The antibody of the kit can be used in an immunoassay, e.g., in a western blot assay, an ELISA, or a radioimmunoassay and the kit may include instructions for use of the antibodies in each of these assay configurations for detecting LMP-2 isoforms (e.g., LMP-2 phosphoprotein isoforms).

Antibodies for Use in the Methods and Kit of the Invention

The antibody that is used in the methods of the invention or as part of the kit of the invention can be a monoclonal or a polyclonal antibody. The monoclonal antibody can be, e.g., LMP2-13 (Fisher Scientific, catalog #04248MI) or MCP421 (Abcam, catalog# ab22672). The polyclonal antibody can be LMP2(N-20) (Santa Cruz Biotechnology, Catalog # sc-16459) or LMP2(C-20) (Santa Cruz Biotechnology, Catalog # sc-16461).

EXAMPLES

Materials and Methods

Patients:

Sjögren's syndrome subjects were recruited over a 5-year period from the Massachusetts General Hospital with full institutional approval and with informed consent. All Sjögren's subjects were in good health, not in renal failure, had neither received kidney transplants nor systemic immunosuppressive therapy, and had longstanding disease of at least 4-years duration. Blood was drawn after informed consent and was drawn into a purple top tube to prevent clotting. The Peripheral blood lymphocytes (PBLs) were prepared by layering the blood over Ficoll for gradient separations. Sjögren's subjects were compared to control subjects with no history of Sjögren's and also no history of any autoimmune disease. All blood was used fresh and was processed the same day for the cellular lysates for later protein detections. After informed consent, all patient and control subjects' blood was drawn into BD Vacutainer tubes (BD) containing acid citrate and dextrose or EDTA Vacutainer tubes (BD)—purple top tubes.

Blood Preparation:

Peripheral blood lymphocytes (PBLs) were isolated by Ficoll. Ficoll Hypaque (Amersham Biotech) gradient centrifugation of fresh human blood was done following the manufacturer's protocol. Red blood cells (RBCs) were further removed by a 5-min (on ice) incubation with $NH_4Cl$ solution (PharMLyse (BD), Franklin Lakes, N.J.).

Preparation of Protein Lysates:

Protein lysates were prepared by placing the Ficoll prepared PBLs into three different kinds of lysate buffers. These lysate buffers were either purchased (Protein Simple) or made directly from urea (Pierce chemical). The ratio of PBLs to lysis buffer was tested to obtain sufficient protein concentrations for testing on western blot assays or for using an automated Western/pI detection system sold by Protein Simple. The lysates were prepared using Bicine/CHAPS lysis buffer and sample diluent, RIPA Lysis buffer, or a urea based lysis buffer (also referred to as "Limei" buffer).

Antibodies to LMP-2:

The polyclonal and monoclonal antibodies used are described above. Control antibodies, including antibodies to control for loading concentrations (e.g., antibodies to housekeeping proteins) and molecular weight, and also antibodies that could detect phosphorylated proteins like ERK1/2 antibodies, are commercially available Western Blot Assay, Automated Western Blots and pI/pH Determinations Using Isoelectric Focusing Assay:

All standard western blot assays were run with 18% gradient (BioRad or Life Technologies). For automated Westerns or charge based separations lysates were run on Simple Western machines on 394 well plates using about 5 ul of concentration protein and duplicates. This system does not require a gel or transfer device but the samples and separations are performed in micro-capillary tubes.

Example 1

Figure 2:
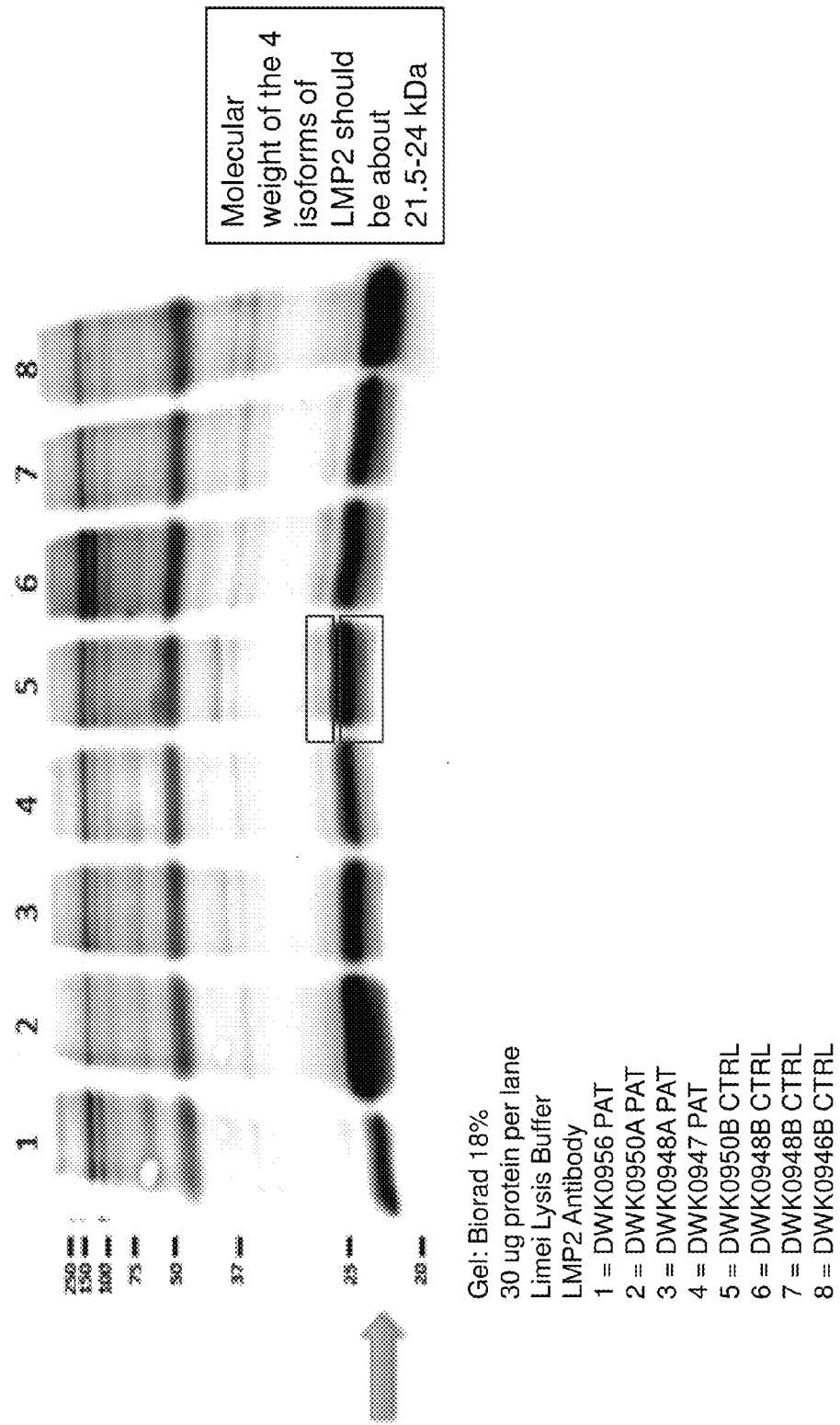
FIG. 2 is an image of a western-blot showing the two bands reactive with anti-LMP-2 that are different between the Sjögren's patient (lanes 1-4) and the control (lanes 5-8) samples.

Western Blot Assay to Detect LMP-2 Isoforms and Reduction of the LMP-2 Isoforms in Sjögren's Syndrome Patients FIG. 2 shows results of a western blot assay performed with lysates of samples from control and Sjögren's syndrome patients. The molecular weight of the four isoforms is predicted to be between 21-24 kD. In agreement with this prediction, the western blot assay shows differences in bands between the Sjögren's and the control samples in this molecular weight range.

Example 2

Figure 3A:
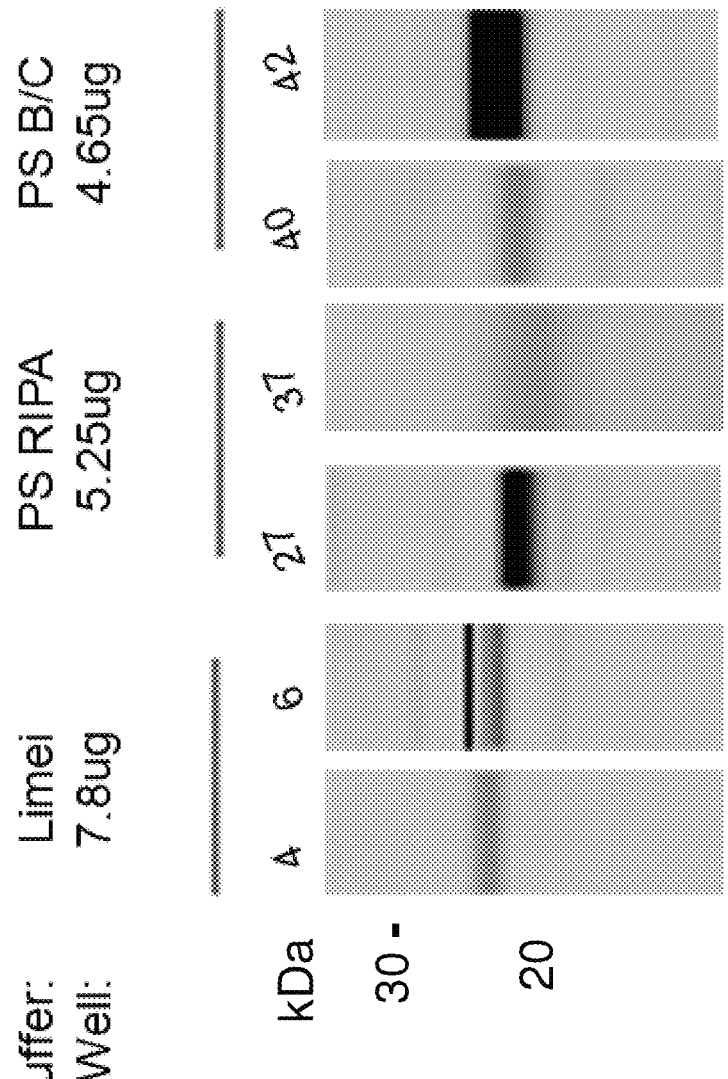
FIG. 3A is an image of a western-blot showing the molecular weight of different bands observed in samples from Sjögren's patients (lanes labeled 4, 37, and 40) and from control patients (lanes labeled 6, 27, and 42) that were processed using three different lysis buffers (Limei, PS RIPA, and PS B/C, respectively).

Optimization of Lysis Conditions and Western Blot Detection of LMP-2 Isoforms with the MCP421 Antibody Three different lysis buffers were tested with control and Sjögren's patient samples. As seen in FIG. 3A and the quantitation in FIG. 3B, differences in banding pattern between 21-24 kD is observed between Sjögren's patients (lanes labeled 4, 37, and 40) and control patients (lanes labeled 6, 27, and 42). The difference is best observed when the "Limei" buffer (a urea-based lysis buffer) and the MCP421 antibody is used.

Example 3

Identification of Four LMP-2 Isoforms by Isoelectric Focusing Assay. Reductions in the Levels of the Four Isoforms are Observed in Sjögren's Sample Lysates Protein diversity can be driven by molecular weights that can vary for proteins with the same or similar sequence. This difference in molecular weight can be due to different mRNA start sites, different splice forms, or variation in amino acid charge. Also, proteins after synthesis can have different phosphorylation patterns that are also influenced by varying splice forms and translation start sites. Therefore an alternative way to differentiate proteins of the same or similar sequence is to measure their charge by pH or pI analyses. This is typically done using isoelectric focusing.

For LMP-2 the predicted molecular weight should be around 221(D. In the human up until now only two isoforms of the protein have been identified which have a molecular weight in the range of 21-23 kD. Based on the protein sequence only select amino acids can be phosphorylated.

Figure 4:
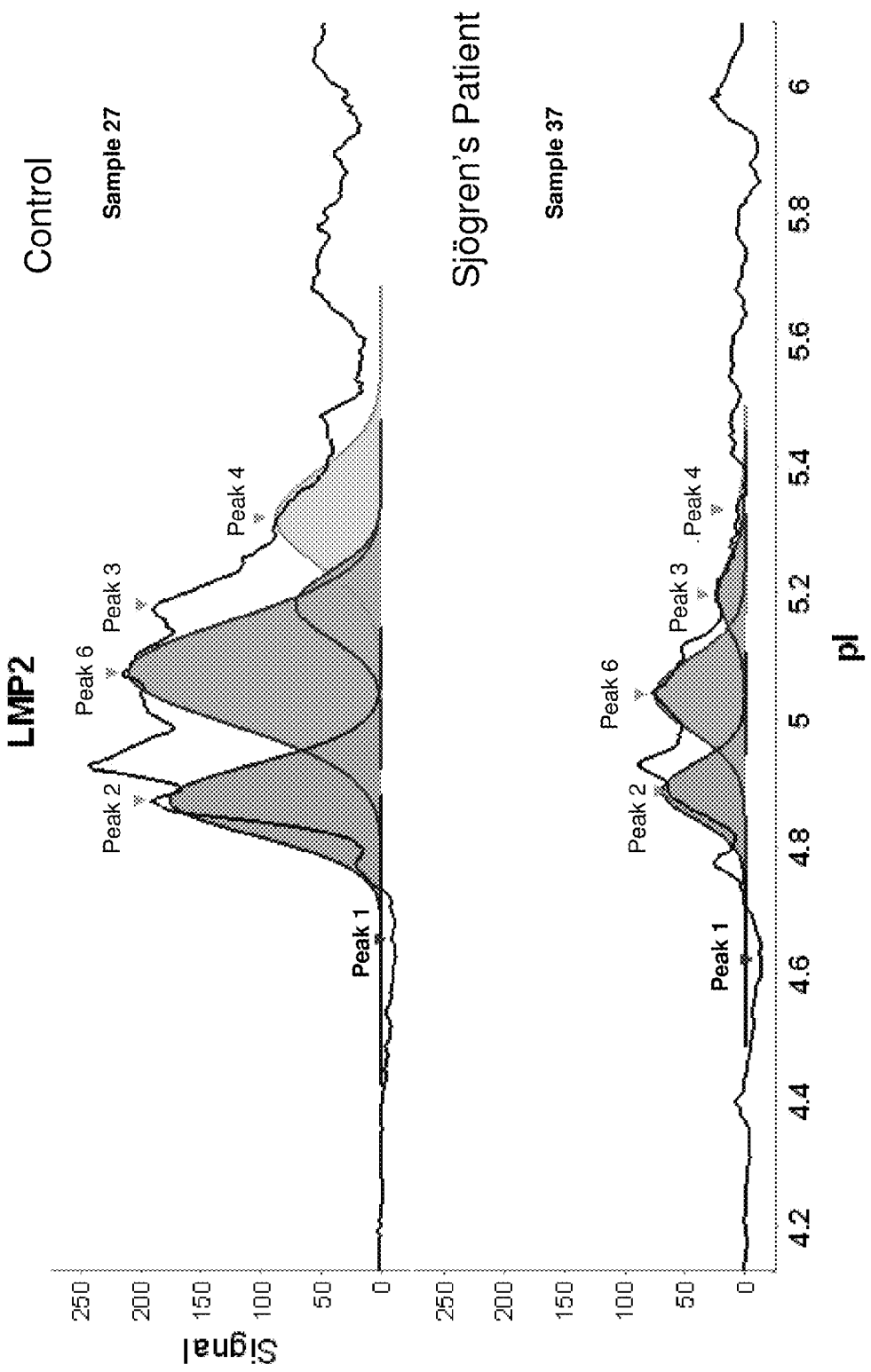
FIG. 4 is an image showing the results of an isoelectric focusing assay that was set up to detect only phosphoproteins performed using lysates prepared from control and Sjögren's patient samples. Samples were run at 1:250 dilution. The detection of the isoforms was performed with the LMP2-13 antibody, a monoclonal antibody to native LMP2 human proteasomes. The image shows a reduction in the levels of the four LMP-2 isoforms in a Sjögren's patient relative to the control sample from a non-Sjögren's patient. These samples were run in 384 well plates using the Simple Protein technology i.e. pI/pH detections in a single gel direction by capillary based isoelectric focusing to resolve various protein phosphorylation states.

PBL lysates were prepared using the Limei buffer or a Bicine/CHAPS lysis buffer. Lysates were subjected to isoelectric focusing and the LMP-2 isoforms were detected with the LMP2-13 antibody. The isoelectric focusing assay can detect 4 LMP-2 isoforms in human PBL lysates. Furthermore, over a 50% reduction in total LMP-2 in PBL lysates in the Sjögren's patient relative to a non-Sjögren's control sample is observed (FIG. 4).

Figure 5:
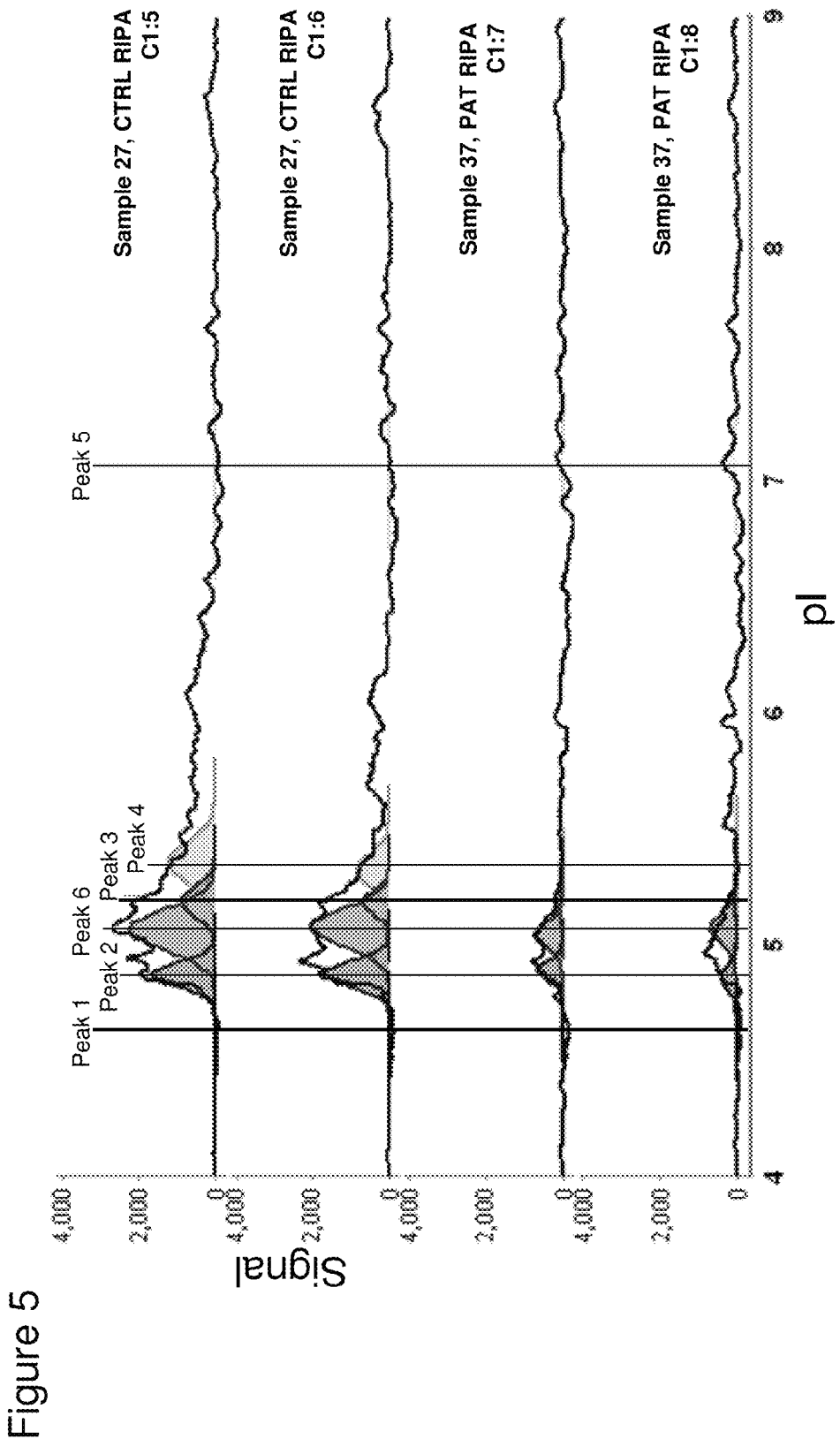
FIG. 5 is an image showing the results of phosphoprotein signaling assay performed using lysates prepared from control and Sjögren's patient samples using RIPA buffer containing inhibitors to prevent the de-phosphorylation of the phosphoproteins. The image shows a reduction in the levels of the four LMP-2 phosphoprotein isoforms in Sjögren's patients relative to the control samples from non-Sjögren's patients. These Sjögren's patients had primary Sjögren's previous diagnosed by the presence of clinical symptoms (dry eyes, dry mouth) presence of autoantibodies (anti-Ro, anti-LA) and positive lip biopsies for lymphocytic infiltrates. Control samples were subjects not only free of Sjögren's symptoms but with negative family histories of autoimmunity.
Figure 6:
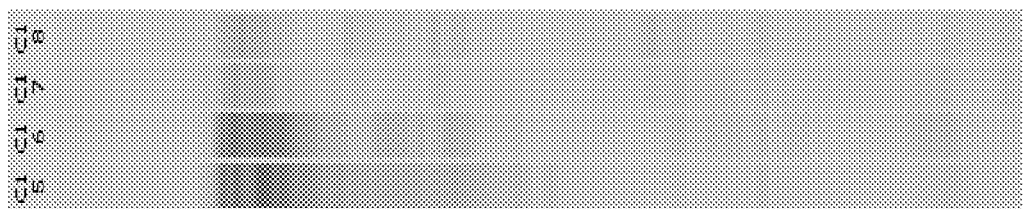
FIG. 6 is an image of a western blot performed after isoelectric focusing of control samples (lanes 5 and 6) and Sjögren's samples (lanes 7 and 8) that were lysed with RIPA buffer. The western blot was contacted with the LMP2-13 antibody.

Similar results are obtained in additional Sjögren's subjects where the PBLs were lysed in RIPA lysis buffer (FIG. 5). Again in this case, the LMP2-13 antibody performed best in detecting the isoforms (FIG. 6).

Example 4

Over-Phosphorylation of ERK in Sjögren's Samples

Figure 7:
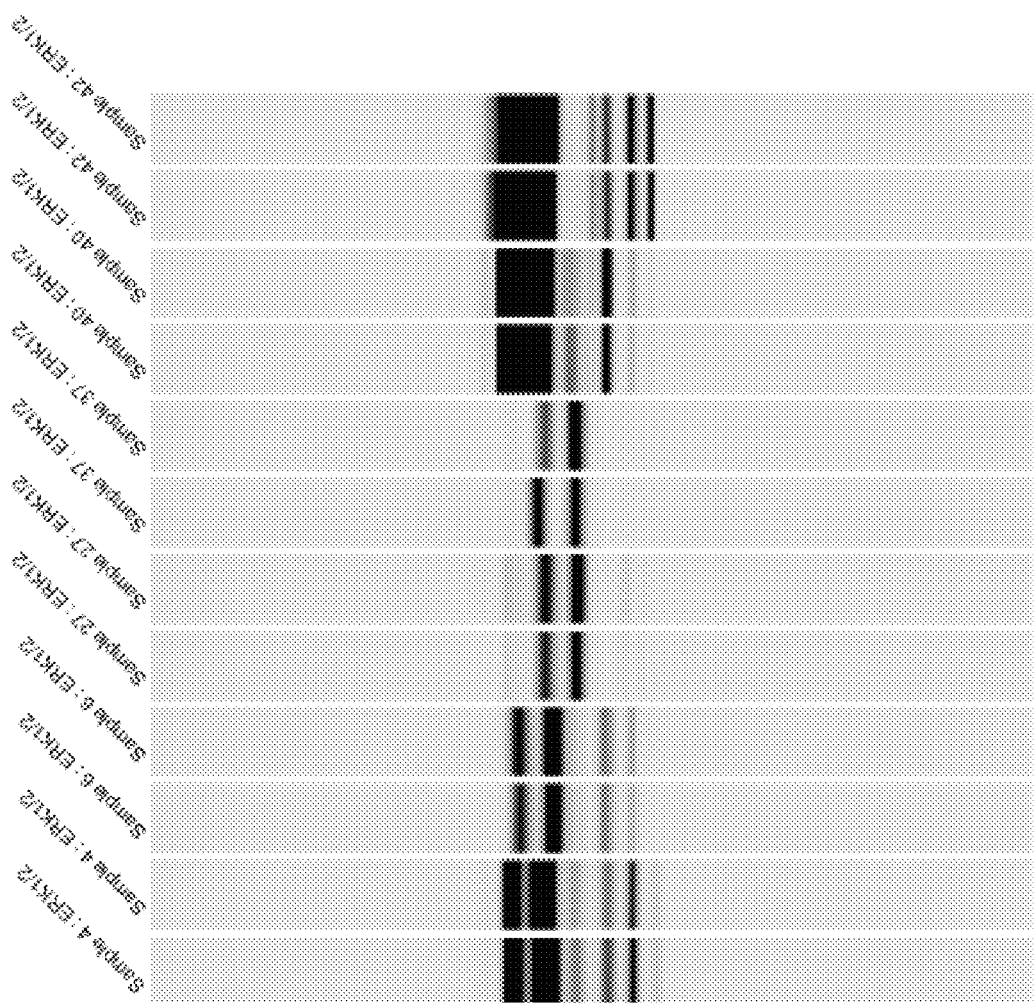
FIG. 7 is an image of a western blot showing that Sjögren's samples (samples 4, 27, and 42) have over phosphorylated ERK compared to control samples (samples 6, 37, and 40). In this experiment, different lysis buffers were tested. Samples 4 and 6 were in the same lysis buffer, samples 27 and 37 were in the same lysis buffer and samples 40 and 42 were in the same lysis buffer. Lysis buffers included bicine/CHAPS lysis buffer and sample diluent, RIPA Lysis buffer and Urea based lysis buffer (Limei buffer) with de-phosphorylation inhibitors.

Sjögren's and control samples prepared with different lysis buffers were separated by isoelectric focusing followed by western blot assay to detect phosphorylated ERK. Samples 4 and 6 were in the same lysis buffer, samples 27 and 37 were in the same lysis buffer and samples 40 and 42 were in the same lysis buffer. As seen in FIGS. 7 and 8, Sjögren's samples (samples 4, 27, and 42) have over phosphorylated ERK compared to control samples (samples 6, 37, and 40).).

Example 5

Optimization of Detection of LMP-2 Isoforms by Isoelectric Focusing

Figure 9:
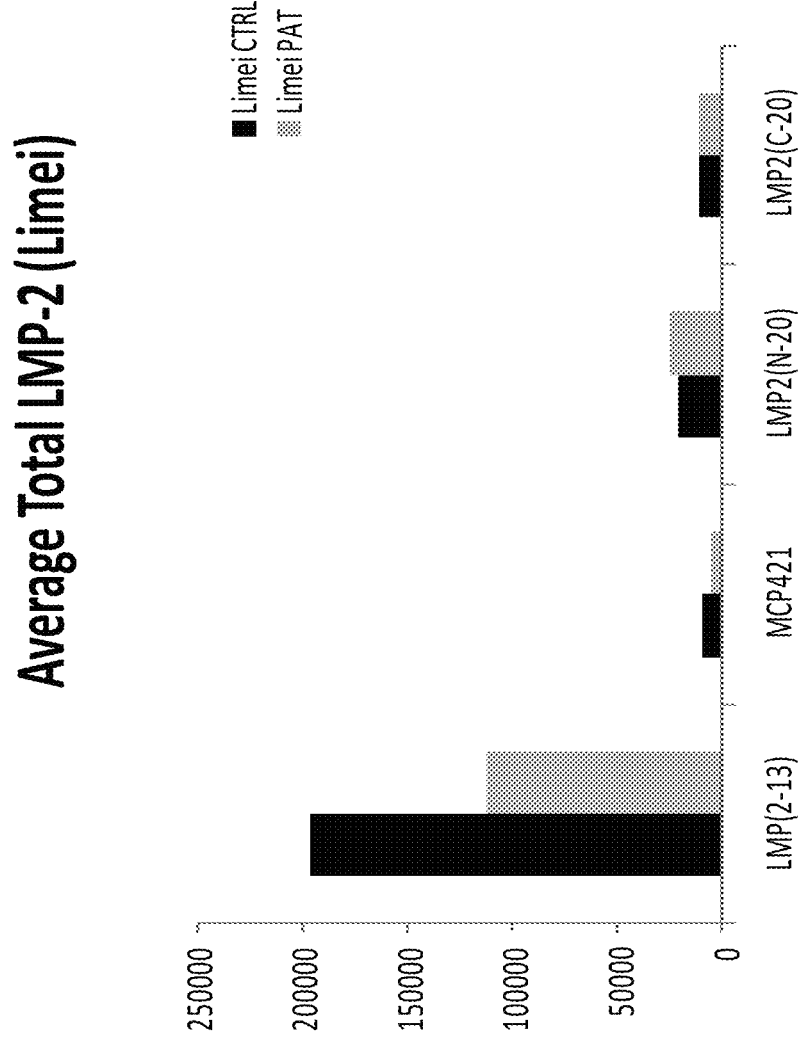
FIG. 9 is a graph showing reduced LMP-2 levels in Sjögren's samples (gray) compared to control subject samples (black).
Figure 10:
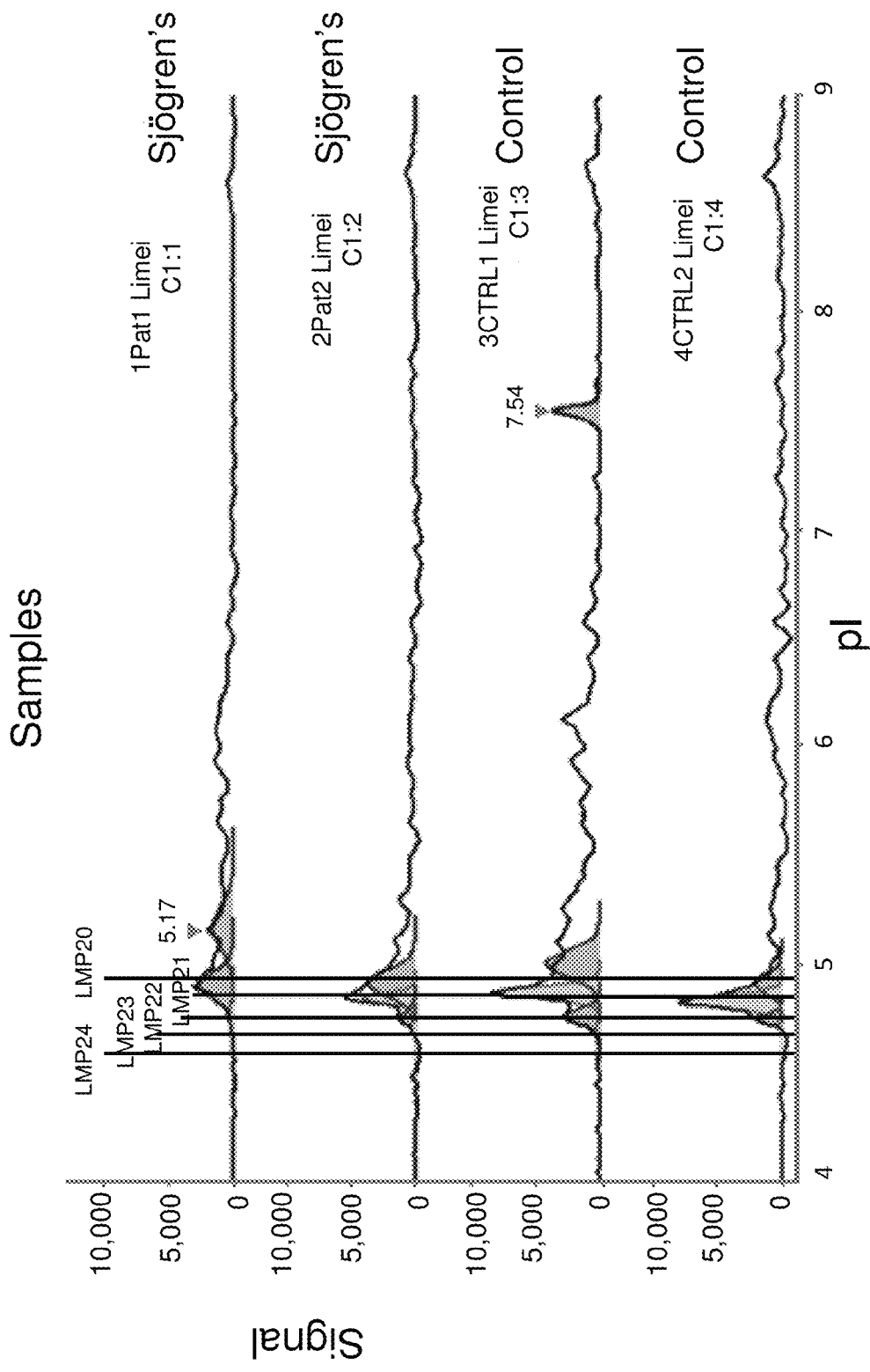
FIG. 10 is an image showing the results of phosphoprotein signaling assay performed using lysates prepared from control and Sjögren's patient samples using Limei buffer. The image shows a reduction in the levels of the five LMP-2 isoforms in Sjögren's patients relative to the control samples from non-Sjögren's patients. These Sjögren's patients had primary Sjögren's previous diagnosed by the presence of clinical symptoms (dry eyes, dry mouth) presence of autoantibodies (anti-Ro, anti-LA) and positive lip biopsies for lymphocytic infiltrates. Control samples were subjects not only free of Sjögren's symptoms but with negative family histories of autoimmunity.

Sjögren's and control PBL lysates were prepared using the Limei buffer and the lysates were separated by isoelectric focusing followed by western blot detection using the different anti-LMP-2 antibodies. As shown in FIGS. 9 and 10, the use of the LMP2-13 monoclonal antibody along with the use of the urea lysis buffer (Limei buffer) and use of the automated method of quantifying the difference in various isoforms using isoelectric focusing shows major differences in LMP-2 isoform levels in Sjögren's patient relative to non-Sjögren's control samples. This experiment demonstrates the optimal experimental conditions that help to observe this difference, and further demonstrates that not all antibodies were equally effective, e.g., antibody MCP421, LMP2(N-20) and LMP2(C-20) were not effective. This is a magnitude difference of over 30% for all subjects studied (n=22).

Example 6

Amount of Phosphoproteins in Different Peaks of the LMP-2 Protein Isoforms

Table 1 below shows a quantitation of the amount of phosphoproteins in different peaks representing the different phosphorylated LMP-2 isoforms and how their amounts are reduced in the Sjögren's samples relative to the control samples.

TABLE 1

|  | LMP20 | LMP21 | LMP22 | LMP23 | LMP24 |
| --- | --- | --- | --- | --- | --- |
| Sjogren's |  |  |  |  |  |
| 1Pat1 Limei | 70126.963 | 0 | 4009.619 | 683.276 | 0.218 |
| 2Pat2 Limei | 80809.18 | 48540.639 | 20015.985 | 440.927 | 0.147 |
| 8PAT1 CHAPS | 0 | 0 | 0 | 70489.451 | 32704.088 |
| 9PAT2 CHAPS | 0.074 | 18189.105 | 24693.066 | 0 | 99244.61 |
| 10PAT3 CHAPS | 60204.153 | 12612.374 | 9915.746 | 8610.076 | 69555.907 |
| 11PAT4 CHAPS | 25805.151 | 45001.275 | 19110.269 | 34059.858 | 8928.566 |
| 12PAT5 CHAPS | 2078.297 | 0 | 0 | 44835.865 | 28020.825 |
| Sum | 239023.818 | 124343.393 | 77744.685 | 159119.453 | 238454.361 |
| Average | 34,146 | 17,763 | 11106 | 22731 | 19779 |
| Controls |  |  |  |  |  |
| 3CTRL1 Limei | 81021.766 | 108810.775 | 41377.964 | 3225.12 | 834.551 |
| 4CTRL2 Limei | 29898.172 | 109192.1 | 17817.895 | 0.105 | 0.112 |
| 5CTRL1 CHAPS | 63277.93 | 87929.929 | 0.256 | 35111.518 | 0 |
| 6CTRL2 CHAPS | 69438.726 | 50586.72 | 30301.856 | 15465.681 | 101483.453 |
| 7CTRL3 CHAPS | 0.127 | 41399.76 | 0 | 78854.169 | 4244.04 |
| Sum | 243636.721 | 397919.284 | 89497.971 | 132656.593 | 106562.156 |
| Average | 48,727 | 79,583 | 17899 | 26531 | 21312 |

Example 7

Assays to Measure Phosphorylation and Ubiquitination of Protein in Sjögren's Patients Relative to Control Patients Sjögren's and control PBL lysates can be used for measuring changes in global phosphorylation and ubiquitination of proteins in the Sjögren's sample relative to the control sample. These measurements can be made using a western blot assay with an anti-phospho antibody or an anti-ubiquitin antibody (both of which are commercially available).

Example 8

Combination Assays for Detecting Changes in LMP-2 Isoform Levels Relative to Changes in General Protein Phosphorylation and Ubiquitination Levels Sjögren's and control PBL lysates can be used for measuring changes in the levels of LMP-2 protein isoform levels in the Sjögren's sample relative to the control sample using the isoelectric focusing and/or immunoassay techniques described herein. These assays can be further combined with at least a second additional assay that measures a "biomarker" characteristic of Sjögren's syndrome. These other assays include, e.g., measuring changes in global cellular phosphorylation, or in the phosphorylation of one or more specific proteins, such as ERK1/2, in a cell or cell population in a sample from a patient suspected of having Sjögren's syndrome, and/or measuring the level of ubiquitinated proteins in a cell or cell population in a sample from a patient suspected of having Sjögren's syndrome, relative to a control sample. This combination of assays utilizes these two or more different "biomarkers" characteristic of Sjögren's syndrome (e.g., a reduction in the level of, or change in the ratio of, one or more LMP-2 isoforms, changes in protein phosphorylation, and changes (e.g., increases) in protein ubiquitination) to diagnose this disease in patients in need thereof.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

All publications and patent applications mentioned in this specification are herein incorporated by reference to the same extent as if each independent publication or patent application was specifically and individually indicated as being incorporated by reference in their entirety.

The invention claimed is:

1. A method for determining the presence of, or a predisposition to develop, Sjögren's syndrome in a human comprising:
   a) measuring the level of an LMP-2 protein isoform in a first sample obtained from said human comprising separating said LMP-2 protein isoform using isoelectric focusing based on pI, wherein said LMP-2 protein isoform has a pI in the range of 4.5-5.5, and detecting said LMP-2 protein with an anti-LMP-2 antibody; and
   b) measuring a change in the level of phosphorylation of one or more proteins in said first sample, or in a second sample from said human, wherein said one or more proteins comprise extracellular signal-regulated protein kinase (ERK);
   wherein a reduction in the level of said LMP-2 protein isoform, relative to a control, and a change in the level of phosphorylation of said one or more proteins, relative to a control, is indicative of the presence of, or a predisposition to develop, Sjögren's syndrome.

2. The method of claim 1, further comprising a molecular weight resolution step.

3. The method of claim 1, wherein said measuring in step b) is performed using an immunoassay.

4. The method of claim 3, wherein said immunoassay is selected from the group consisting of western blot assay, ELISA, pH or pI gradient electrophoresis, gel electrophoresis, or radioimmunoassay.

5. The method of claim 1, wherein said anti-LMP2 antibody is a monoclonal or polyclonal antibody.

6. The method of claim 5, wherein said monoclonal antibody is one of LMP2-13.

7. The method of claim 1, wherein step a) comprises measuring the level of two, three, four, or more of said LMP-2 protein isoforms.

8. The method of claim 1, wherein said LMP-2 protein isoform is differentially phosphorylated.

9. The method of claim 1, wherein said reduction in the level of said LMP-2 protein isoform is at least a 20% reduction.

10. The method of claim 1, wherein said first or second sample is a body tissue or fluid comprising lymphocytes or a body fluid selected from blood, saliva, and lymph.

11. The method of claim 1, further comprising measuring an increase in the level of ubiquitination of one or more proteins in said first or second sample relative to a control.

12. The method of claim 1, wherein said change in the level of phosphorylation of said one or more proteins is an increase in phosphorylation.

13. The method of claim 1, wherein said human is suspected of having Sjögren's syndrome.

14. The method of claim 1, wherein said control is generated using a sample obtained from a human without Sjögren's syndrome.

15. The method of claim 1, wherein said measuring in step b) is performed by contacting said one or more proteins with a phosphophorylation site-specific antibody.

16. The method of claim 12, wherein said change in the level of phosphorylation is an increase of at least 10%.

17. The method of claim 1, wherein said measuring in step b) is performed by contacting said one or more proteins with an ERK-specific antibody.

18. The method of claim 11, wherein said increase in the level of ubiquitination is detected with an ubiquitination site-specific antibody.

19. The method of claim 11, wherein said increase in the level of ubiquitination of said one or more proteins is an increase of at least 10%.

20. The method of claim 1, wherein said measuring steps a) and b) are performed using said first sample.

* * * * *